United States Patent
Tat et al.

(10) Patent No.: US 7,584,062 B1
(45) Date of Patent: Sep. 1, 2009

(54) SUB-WAVELENGTH ULTRASOUND CHARACTERIZATION OF COMPOSITE MATERIAL

(75) Inventors: Hong H. Tat, Redmond, WA (US);
Richard H. Bossi, Renton, WA (US);
Yuan-Jye Wu, Issaquah, WA (US);
John-Paul N. Sabino, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/143,662

(22) Filed: Jun. 20, 2008

(51) Int. Cl.
*G01B 5/02* (2006.01)
(52) U.S. Cl. .............................. 702/39; 73/597; 73/639; 367/99; 702/171
(58) Field of Classification Search .................. 702/39, 702/103, 119, 124, 159, 170, 171; 73/597, 73/639; 324/216, 240; 367/13, 99
See application file for complete search history.

(56) References Cited

U.S. PATENT DOCUMENTS

| | | | | |
|---|---|---|---|---|
| 4,412,315 | A | * | 10/1983 | Flournoy ...................... 367/99 |
| 5,404,755 | A | * | 4/1995 | Olson et al. ................... 73/639 |
| 7,246,522 | B1 | * | 7/2007 | Diaz et al. .................... 73/597 |

OTHER PUBLICATIONS

Bar-Cohen et al., "Acoustic-Backscattering Imaging of Subcritical Flaws in Composites", Materials Evaluation 40, 1982, pp. 970-975.
Candes et al., "Stable Signal Recovery from Imcomplete and Inaccurate Measurements", Communications on Pure and Applied Mathematics, 59(8), Aug. 2006, 17 pgs.
Cramer, "Thermal Nondestructive Evaluation Report—Inspection of the Refurbished Manipulator Arm System in the Manipulator Development Facility of Johnson Space Center Jan. 10-12, 2001", NASA Document TM-2002-211732, Jul. 2002, 19 pgs.
Dayal, "Fabrication and Ultrasonic Nondestructive Evaluation of Wavy Composites", Vibro-Acoustic Characterization of Materials and Structures, NCA-vol. 14, 1992, pp. 215-219.
Donoho, "Compressed Sensing", IEEE Trans on Information Theory, 52(4), Apr. 2006, 34 pgs.
Highsmith et al., "The Influence of Fiber Waviness on the Compressive Behavior of Unidirectional Continuous Fiber Composites", Composite Materials: Testing and Design, 10th vol, ASTM STP 1120, 1992, 17 pgs.
Joyce et al., "A Technique for Characterizing Process-Induced Fiber Waviness in Unidirectional Composite Laminates-Using Optical Microscopy", Journal of Composite Materials, 31, No. 17, 1997, 35 pgs.

(Continued)

*Primary Examiner*—John H Le
(74) *Attorney, Agent, or Firm*—Lee & Hayes, PLLC

(57) ABSTRACT

An ultrasonic stimulus pulse is emitted incident to a laminar structure and recorded as pulse data. Echoes resulting from the stimulus pulse are recorded as echo data. One or more vectors are derived by way of time-shifting the recorded pulse data by respective amounts and a matrix Φ is defined including the one or more vectors. An echo vector Y is defined using the recorded echo data. A solution vector X is determined in accordance with: Y=Φ*X, typically within a predetermined tolerance. B-scan display or other analysis of one or more distinct solution vectors enables user and/or automated identification and measurement of any anomalies within the laminate material.

20 Claims, 6 Drawing Sheets

OTHER PUBLICATIONS

Kazys et al., "Ultrasonic Detection and Characterization of Delaminations in Thin Composite Plates Using Signal Processing Techniques", Ultrasonics, vol. 35, No. 5, 1997, 17 pgs.

Kazys et al., "Ultrasonic Phase Imaging of Multilayred Structures", Ultragarsas Journal, vol. 26, No. 1, 1996, 3 pgs.

Murri et al., "Defects in Thick Composites and Some Methods to Locate Them", Review of Progress in Quantitative Nondestructive Evaluation, vol. 10B, 1991, pp. 1583-1590.

O'Brien et al., "Recovery of a Sparse Spike Time Series by L1 Norm Deconvolution", IEEE Transactions on Signal Processing, vol. 42, Issue 12, Dec. 1994, 13 pgs.

Pagodinas, "Ultrasonic Signal Processing Methods for Detection of Defects in Composite Materials", Ultragarsas Journal, vol. 45, No. 4, 2002, 8 pgs.

Pandey et al., "Mechanisms of Wrinkle Formation During the Processing of Composite Laminates", Composite Science and Technology, 59, Issue 3, Feb. 1999, pp. 405-417.

Wooh et al., "Characterization of Fiber Waviness in Thick Composites Based on an Ultrasonic Ray Tracing Model", Review of Progress in Quantitative Nondestructive Evaluation, vol. 13B< 1994, pp. 1291-1298.

Wooh et al., "Wave Propagation in Composite Materials with Fibre Waviness", Ultrasonics, vol. 33, No. 1, 1995, pp. 3-10.

Yurgartis, "Measurement of Small Angle Fiber Misalignments in Continuous Fiber Composites", Composites Science and Technology, 30, 1992, pp. 279-293.

* cited by examiner

SUB-WAVELENGTH ULTRASOUND CHARACTERIZATION OF COMPOSITE MATERIAL

FIELD OF THE DISCLOSURE

The field of the present disclosure relates to non-destructive testing, and more specifically, to ultrasonic analysis of laminate materials.

BACKGROUND OF THE DISCLOSURE

Non-destructive testing is used in numerous areas of endeavor. One form of non-destructive testing uses sound waves or pulses, generally in the ultrasonic region of the spectrum. In a typical instance, an outgoing pulse (or stimulus) is produced incident to a structure under analysis. Echoes resulting from the pulse are then recorded and analyzed in order to determine structural layering, topography, defects and other characteristics.

Generally, it is necessary to use ultrasonic pulses (stimuli) having wavelengths shorter than the layer thicknesses of the material being tested in order to accurately analyze the resulting echoes. However, shorter ultrasonic wavelengths do not penetrate laminate materials to the same depths as do longer wavelengths. Therefore, improved techniques and equipment for ultrasonic testing of laminate materials using longer ultrasonic wavelengths would have desirable utility.

SUMMARY

One or more embodiments of the present disclosure describe methods for recording an ultrasonic pulse emitted incident to a laminar structure. The recorded pulse data is time shifted by respective amounts to define a plurality of pulse vectors. The pulse vectors are then arranged (raw or processed) so as to define a pulse matrix "Φ" (Phi). Echoes resulting from the ultrasonic pulse are recorded and used (raw or processed) to construct an echo vector "Y". An automated search is performed to find a solution vector "X" in accordance with the relationship: $Y=\Phi*X$. A plurality of feasible vectors are typically generated and compared during the automated search process until a sparse (i.e., minimal magnitude) solution vector X is found. The foregoing method can be repeated any number of times in order to affect a comprehensive scan of the laminar entity. Thereafter, the resulting solution vectors X are graphically plotted by way of B-scan display and used to identify and/or measure any wrinkles, voids, or other inconsistencies in the laminar structure. Systems and apparatus configured to implement the methods of the present teachings are also provided.

In one implementation, a method is performed at least in part by a computer. The method includes recording pulse data corresponding to an ultrasonic pulse emitted by a transducer, and recording echo data resulting from the ultrasonic pulse. The method also includes defining a matrix "Φ", the defining including time-shifting the pulse data is time-shifted by pre-determined amounts. The method further includes deriving an echo vector "Y" from the echo data, and determining a solution vector "X" in accordance with an expression: $Y=\Phi*X$. The method additionally includes presenting the solution vector X as a B-scan display.

In another implementation, a system comprises a memory and a processor. The system is configured to record pulse data corresponding to an ultrasonic pulse. The system is also configured to record echo data corresponding to one or more echoes resulting from the ultrasonic pulse. The system is additionally configured to define a matrix "Φ", which includes time-shifting the pulse data by predetermined amounts. The system is also configured to derive an echo vector "Y" from the recorded echo data. The system is also configured to determine a solution vector "X" in accordance with the expression: $Y=\Phi*X$. The system is further configured to present the solution vector "X" as a B-scan display.

In yet another implementation, an apparatus comprises electronic circuitry. The apparatus is configured to derive one or more vectors including time-shifting a recorded pulse data by respective amounts, and to define a matrix "Φ" including the one or more vectors. The apparatus is also configured to derive an echo vector "Y" from a recorded echo data. The apparatus is further configured to determine a solution vector "X" in accordance with the expression: $Y=\Phi*X$. The solution vector X is stored at least temporarily in a memory of the apparatus.

In another implementation, a computer-readable storage media includes a program code. The program code is configured to cause one or more processors to derive one or more vectors including time-shifting a recorded pulse data by respective amounts. The program code is also configured to cause the one or more processors to define a matrix "Φ" including the one or more vectors, and to derive an echo vector "Y" from a recorded echo data. The program code is further configured to cause the one or more processors to determine a solution vector "X" in accordance with the expression: $Y=\Phi*X$, such that the solution vector X is stored at least temporarily in a memory accessible by the one or more processors.

The features, functions, and advantages that are discussed herein can be achieved independently in various embodiments of the present disclosure or may be combined various other embodiments, the further details of which can be seen with reference to the following description and drawings.

BRIEF DESCRIPTION OF THE DRAWINGS

Embodiments of systems and methods in accordance with the teachings of the present disclosure are described in detail below with reference to the following drawings.

DETAILED DESCRIPTION

The present disclosure teaches systems and methods for implementing long-wavelength ultrasonic testing and analysis of a laminar structure. Many specific details of certain embodiments of the disclosure are set forth in the following description and in FIGS. 1-7 to provide a thorough understanding of such embodiments. One skilled in the art, however, will understand that the disclosure may have additional embodiments, or that the disclosure may be implemented without several of the details described in the following description.

Illustrative Operating Environment

Figure 1:
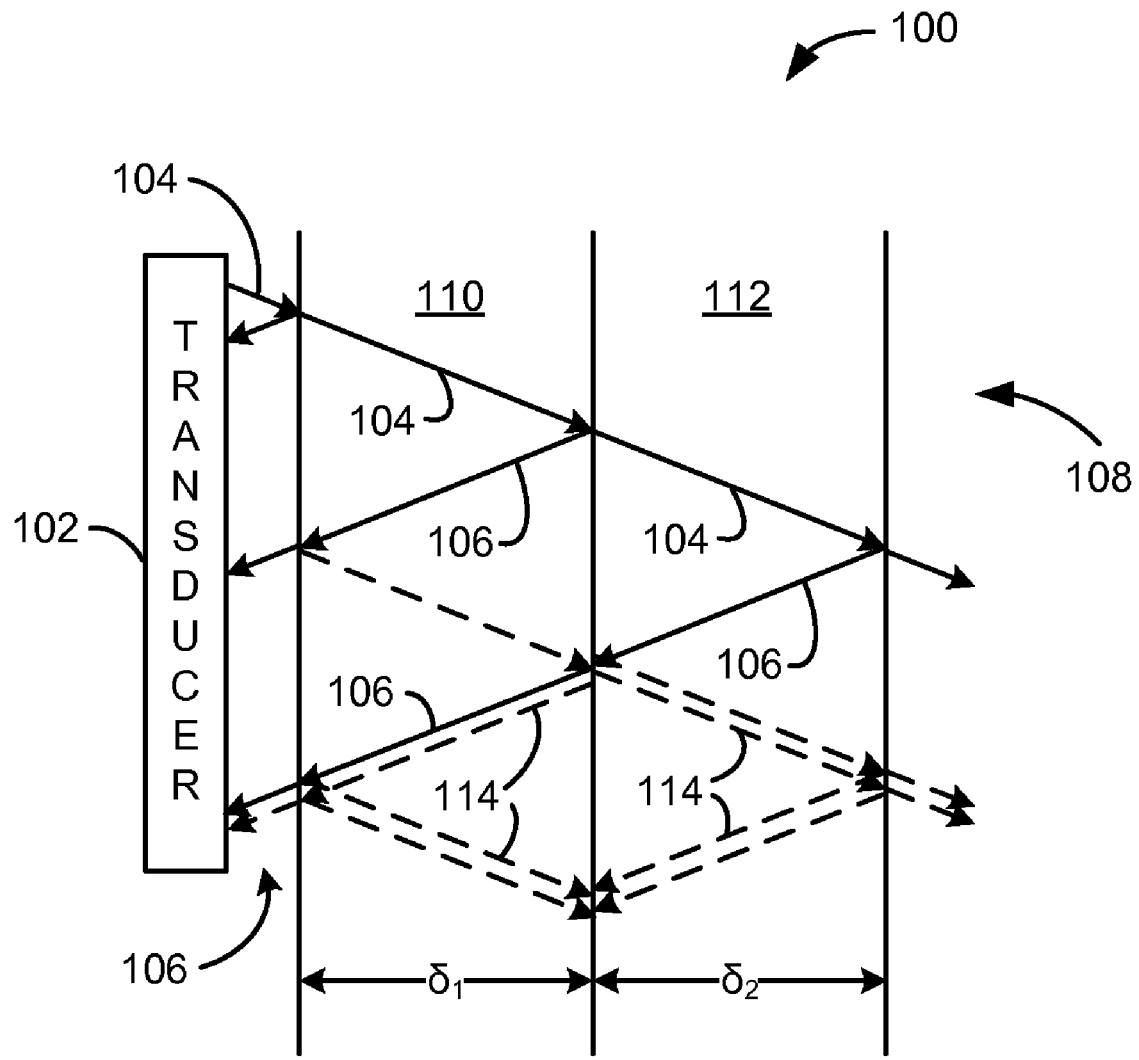
FIG. 1 is a diagrammatic view of an ultrasonic testing scenario according to known techniques.

FIG. 1 is a diagrammatic view of an ultrasonic testing scenario 100. The scenario 100 is illustrative and non-limiting, and is generally known in the related arts. The scenario 100 includes a transducer 102. The transducer 102 is configured to produce (i.e., emit) an ultrasonic pulse 104. The transducer 102 is further configured to receive (i.e., detect) ultrasonic echo signals 106 and to provide corresponding electrical signals (refer to FIG. 2). The scenario 100 also includes a laminate material 108 comprising a first layer 110 and a second layer 112. The first and second layers 110 and 112 are defined by thicknesses 61 and 62, respectively. While only two layers 110 and 112 are shown in the interest of simplicity, it is to be understood that other laminar materials having essentially any number of layers can be analyzed by way of ultrasonic testing.

Under typical operation, the transducer 102 emits an ultrasonic pulse 104 incident to the laminate material 108. Respective echoes 106 are reflected back from the surfaces and interfaces of the layers 110 and 112. The respective echoes 106 are detected by the transducer 102, which responds by producing corresponding time-domain electrical signals. The electrical signals from the transducer 102 are then digitized and recorded as echo data by instrumentation (refer to FIG. 7) coupled to the transducer 102. Furthermore, it is noted that internal reflections (echoes) 114 occur within the laminate material 108. Some of these internal echoes 114 are detected by the transducer 102 as echoes 106, while still others of the echoes 114 pass completely through the material or are internally absorbed. Thus, only a portion of the stimulus pulse 104 energy is recovered by way of the echoes 106.

Figure 2A:
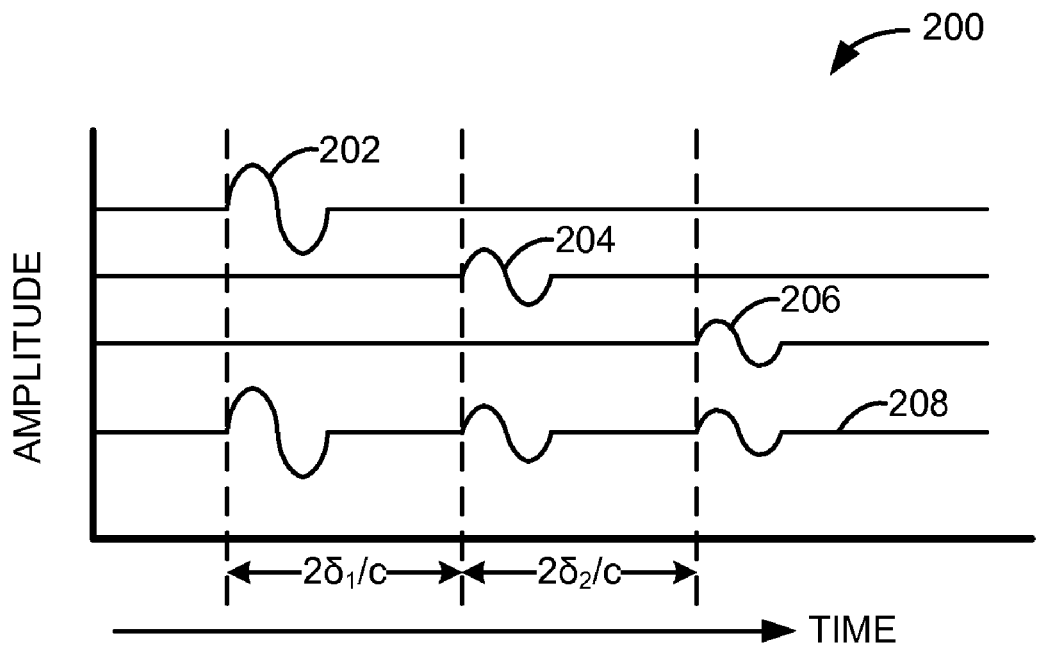
FIG. 2A is a signal timing diagram according to known techniques.

FIG. 2A is a signal timing diagram 200 including illustrative echo signals. The diagram 200 includes a first, a second and a third contributing echo 202, 204 and 206, respectively. The first echo 202 represents an ultrasonic pulse reflection off a surface adjacent to a transducer (e.g., 102) providing a stimulus pulse. In turn, the second echo 204 represents a reflection off of an interface between layers internal to a laminate material (e.g., 108). Finally, the third echo 206 represents a reflection off of the back surface of the laminate material distal to the transducer providing the stimulus pulse. The sum of the echoes 202-206 are detected (i.e., observed) by the corresponding transducer (e.g., 102), which in turn provides a corresponding electrical time-domain signal 208.

It is noted that the echo signals 202-206 are of regular sinusoidal form and represent echoes resulting from an ultrasonic pulse having a wavelength shorter than the respective layer thicknesses of the laminate material (e.g., 108) under analysis. As such, the echo signals 202-206 are readily distinguishable from one another and their individual characteristics (e.g., amplitude, period, etc.) can be subject to reliable analysis. It is further noted that the constant "c" designates wave propagation speed within the laminate structure.

Figure 2B:
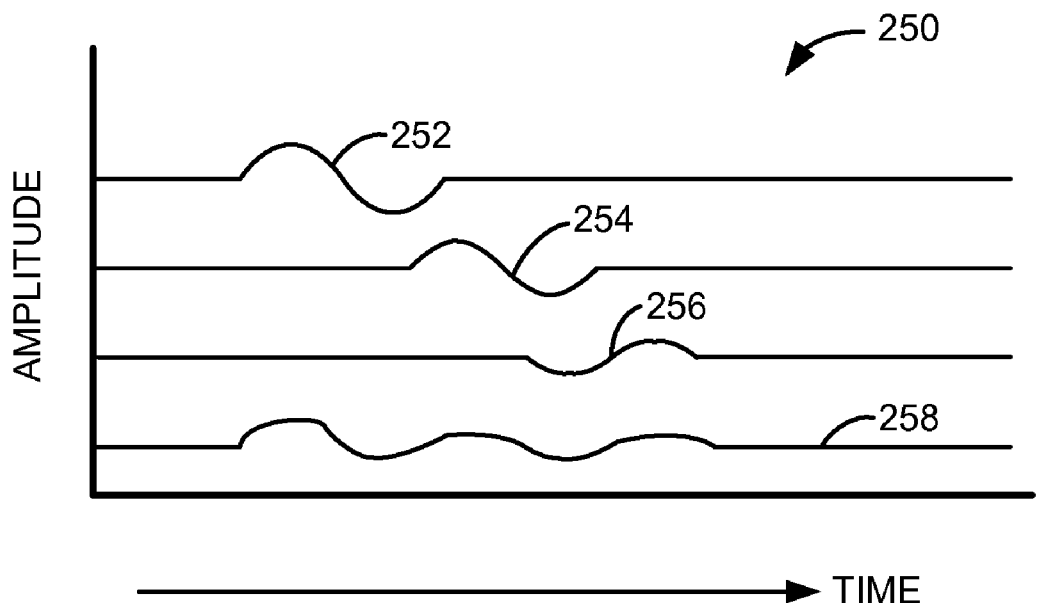
FIG. 2B is another signal timing diagram according to known techniques.

FIG. 2B is a signal timing diagram 250 including illustrative echo signals. FIG. 2B includes a first, a second and a third contributing echo 252, 254 and 256, respectively. The first echo 252 represents an ultrasonic pulse reflection off a surface adjacent to a transducer (e.g., 102) providing a stimulus pulse. The second echo 254 represents a reflection off of an interface between layers internal to a laminate material (e.g., 108). The third echo 256 represents a reflection off of the back surface of the laminate material distal to the transducer providing the stimulus pulse. The echo signals 252-256 are detected (i.e., observed) by the corresponding transducer (e.g., 102), which provides a corresponding electrical time-domain signal 258.

It is important to note that the echo signals 252-256 are the result of an ultrasonic pulse (i.e., stimulus) having a wavelength greater than the respective layer thicknesses of the laminate material (e.g., 108) under analysis. The ultrasonic pulse can, in some implementations, have a wavelength longer than twice the thickness of one or more of the layers of the laminate material under test. Also, while the echo signals 252-256 are of generally sinusoidal form, the echo waveforms 252-256 at least partially overlap one another with respect to their arrival time at the transducer. The overall time-domain signal 258 provided by the transducer (e.g., 102) includes the summation of those overlapping signal 252-256 portions. As a result, the individual echoes 252-256 are not readily distinguishable within the electrical signal 258, and analysis of their respective characteristics is difficult or impossible under known techniques.

First Illustrative Method

Figure 3:
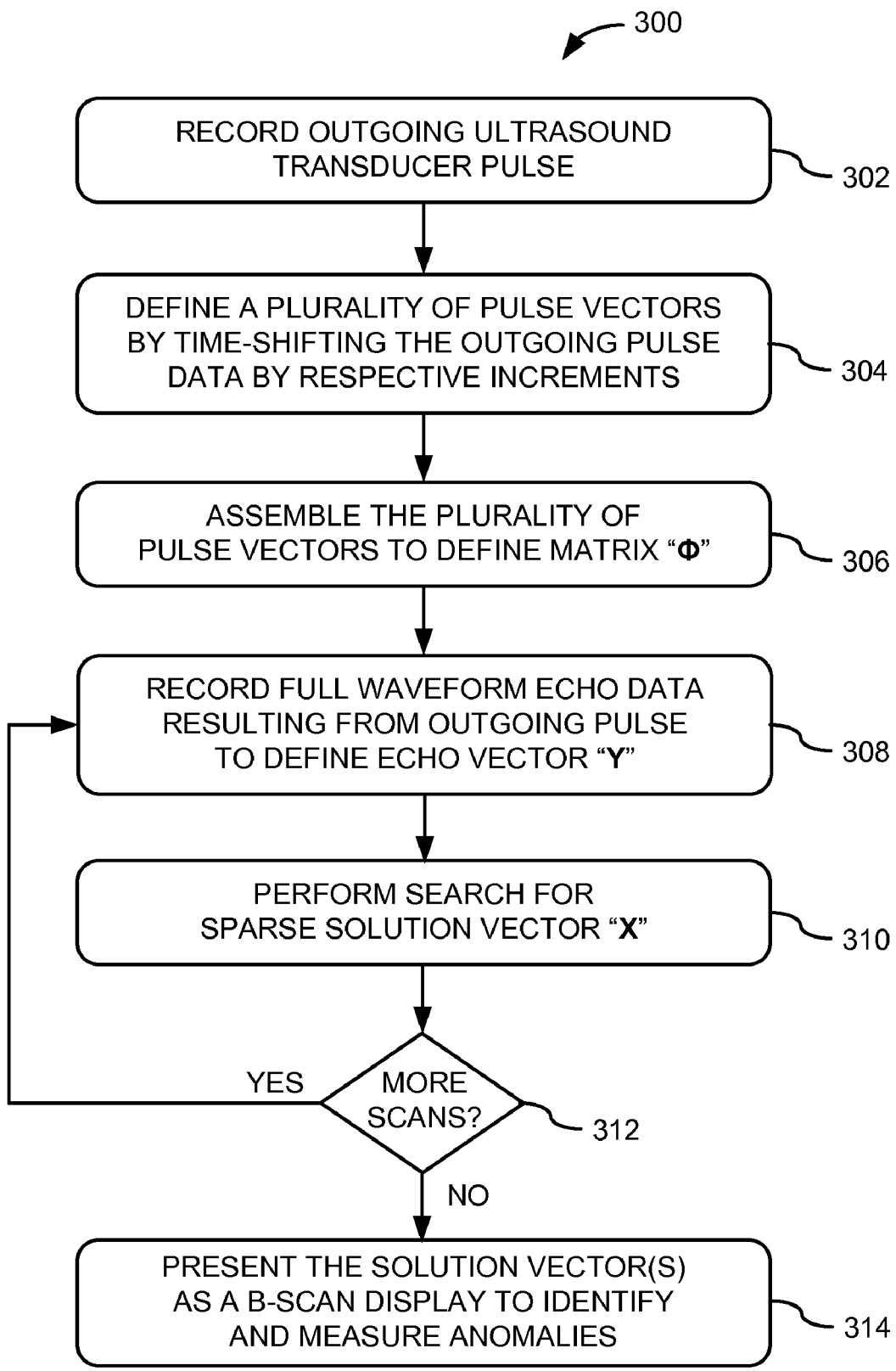
FIG. 3 is a flow diagram depicting a method in accordance with an implementation.

FIG. 3 is a flow diagram 300 depicting a method in accordance with one implementation of the present teachings. The diagram 300 depicts particular method steps and order of execution. However, it is to be understood that other implementations can be used including other steps, omitting one or more depicted steps, and/or progressing in other orders of execution without departing from the scope of the present teachings. The method of the diagram 300 while be described with reference to FIGS. 1 and 4 in the interest of understanding.

At 302, a transducer (e.g., 102) provides a stimulus (i.e., outgoing) pulse incident to a multi-layer, laminate material. In one illustrative and non-limiting instance, the laminate material consists of several plies of individual thin-layer materials laid down as successive, contacting layers. Other laminate material structures can also be considered. In one or more illustrative instances, the stimulus pulse is defined by a wavelength that is greater than twice the thickness of one or more of the layers of the laminate material subject to the pulse. In any case, the outgoing pulse is digitized and recorded as transducer pulse data.

At 304, the outgoing pulse data is shifted by respective and incremental amounts so that a plurality of pulse vectors are defined. Any number of pulse vectors can be defined in this way such that an incrementally related set of vectors is formed. The outgoing pulse data can also be filtered, smoothed, and/or otherwise processed in accordance with known signal processing techniques prior to defining the plurality of pulse vectors.

At 306, the pulse vectors defined at 304 above are assembled in a chronologically advancing order so as define a matrix "Φ" (phi). Reference is made to the matrix Φ of FIG. 4. While the individual column vectors of the matrix Φ are depicted as waveforms in FIG. 4, one of skill in the signal processing or related arts can appreciate that the actual vectors are comprised of suitable numerical values representing the digitally sampled (and possibly processed) outgoing pulse.

At 308, the full waveform echo signal is detected by the transducer (e.g., 102), converted to a corresponding time-domain electrical signal, digitized, and recorded. This resulting recorded, digitized, data is used to define an echo vector "Y". The echo data can be filtered, smoothed and/or otherwise processed according to known signal processing techniques prior to defining the echo vector Y. Reference is made to the echo vector Y of FIG. 4. The echo vector Y is depicted in FIG. 4 as a waveform, but is understood to actually comprise suitable numerical values (quantification) of the digitally sampled (and possibly processed) echo waveform signal (e.g., 258).

At 310, an automated, computerized search is performed, resulting in a sparse solution vector "X", in accordance with the relationship:

$$Y=\Phi^*X \quad \text{(Equation 1)}$$

Figure 4:
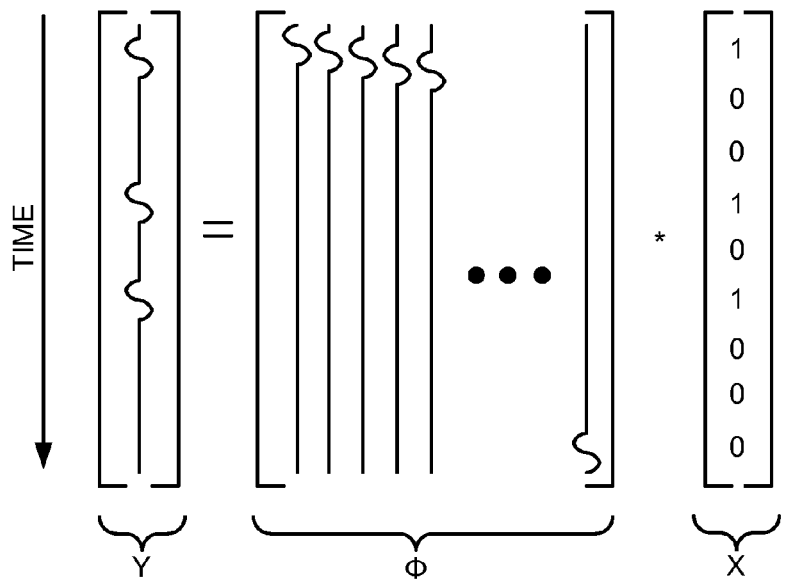
FIG. 4 is a diagrammatic view depicting a mathematical relationship according to the present teachings.

This relationship is graphically depicted in FIG. 4. Typically, some number (a finite set) of solution vectors $x_n$ are determined that satisfy Equation 1 within an acceptable tolerance. However, the particular vector $x_n$ which is the most "sparse" is selected and is designated as the solution vector X. Further elaboration on the generation and selection of the solution vector X is provided hereinafter with respect to FIG. 5. In any case, the sparse solution vector X is selected and the method proceeds to 312.

At 312, it is determined if additional scans of (i.e., passes over) the laminate structure under analysis are required and/or desired. If more scans are required/desired, then the method returns to 308 above, wherein another outgoing pulse is provided and echo data are recorded and processed according to the present teachings. If no more scans are required/desired, then the method proceeds to 314 below.

At 314, a B-scan display of the sparse solution vector (or vectors, if multiple scans were made) is performed by way of suitable electronic display and/or imaging equipment. The B-scan display format is familiar to one having ordinary skill in the non-destructive testing arts. Information regarding B-scan display can be found in: *NDT Handbook*, second edition, Birks et al. (technical editors), American Society for Nondestructive Testing, Columbus, Ohio, 1991. Further information can also be found in: *Ultrasonic Testing of Materials*, second edition, Krautkramer et al., Berlin, N.Y., Springer-Verlag, 1977. Greater elaboration regarding B-scan displays is not needed for purposes herein. The B-scan display is then scrutinized by a user and/or automated means for purposes of identifying and measuring any anomalies within the laminate material under analysis. At this point, a typical, single operative instance of the method of diagram 300 is considered complete.

FIG. 4, as discussed above, illustrates a mathematical relationship according to the present teachings.

Second Illustrative Method

Figure 5:
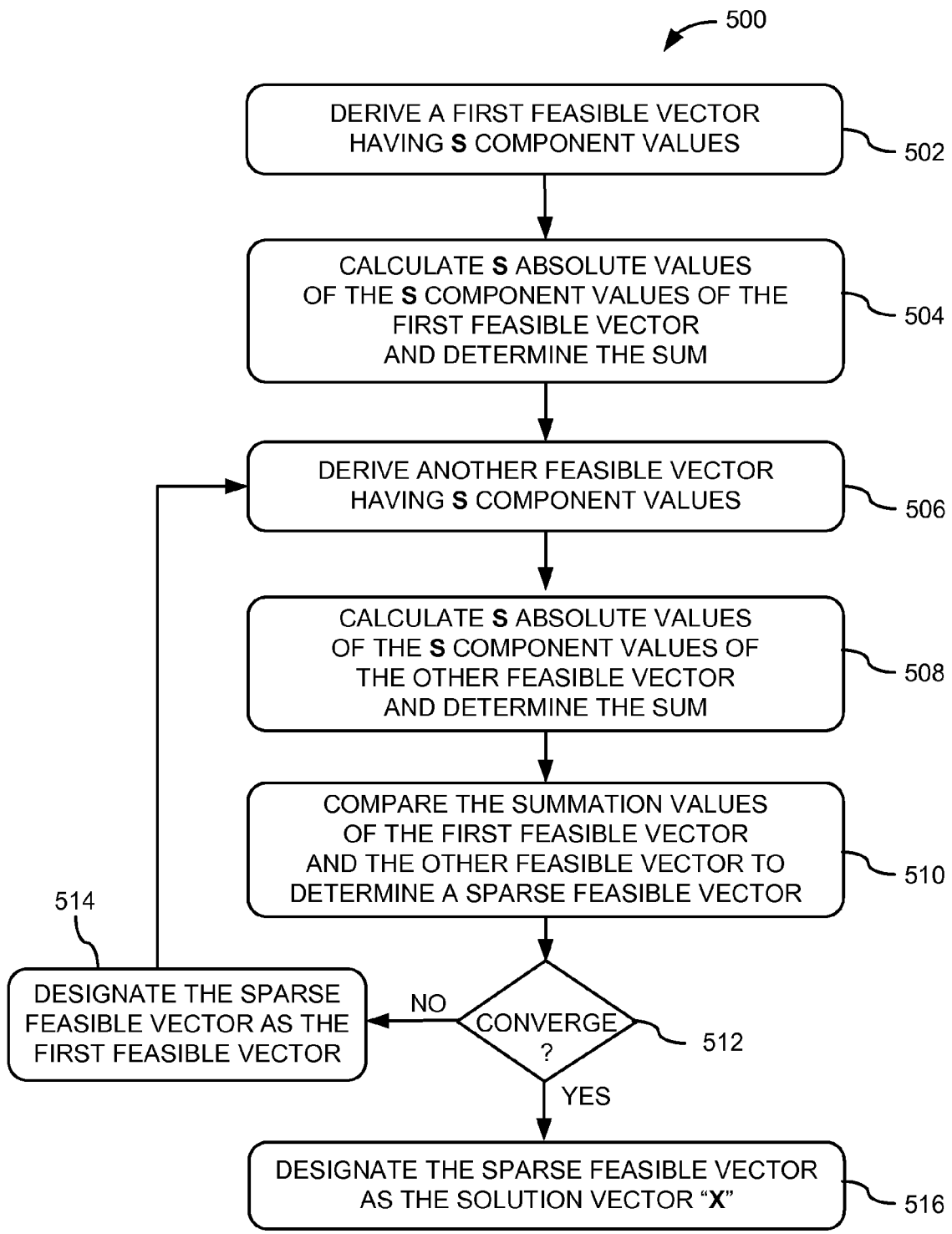
FIG. 5 is a flow diagram depicting a method in accordance with an implementation.

FIG. 5 is a flow diagram 500 depicting a method in accordance with one implementation of the present teachings. The diagram 500 depicts particular method steps and order of execution. However, it is to be understood that other implementations can be used including other steps, omitting one or more depicted steps, and/or progressing in other orders of execution without departing from the scope of the present teachings. The diagram 500 depicts one illustrative and non-limiting method for determining a sparse solution vector as that term was introduced above. In one non-limiting implementation, the method of diagram 500 is performed at 310 of FIG. 3.

At 502, a first feasible vector is derived in accordance with Equation 1 above. As used herein, the term "feasible vector" refers to a vector which satisfies Equation 1 within a predetermined (i.e., user defined) tolerance. In any case, the first feasible vector includes S component (element) values. In one non-limiting example, it is assumed that a feasible vector is derived having nine component values (i.e., S=9). It is noted that the number of components S is equal to the number of pulse vectors (i.e., column vectors) in the corresponding matrix $\Phi$.

At 504, the absolute value of each of the S component values of the first feasible vector is calculated. The S absolute values are then summed to determine a summation value corresponding to the first feasible vector.

At 506, another feasible vector is derived in accordance with Equation 1 above. The other feasible vector, like the first feasible vector, also includes S component (element) values.

At 508, the absolute value of each of the S component values of the other feasible vector is calculated. The S absolute values are then summed to determine a summation value corresponding to the other feasible vector.

At 510 the summation values of the first feasible vector and the other feasible vector are compared. The feasible vector with the lower summation value is selected and designated as the sparse feasible vector.

At 512, it is determined if the two most recently compared summation values indicate convergence within some tolerance. That is, the summation values are compared to determine if the differential between them is within some predetermined and user-definable value. If convergence is determined, the method proceeds to 516 below. If convergence is not determined, then the method proceeds to 514 below.

At 514, the sparse feasible vector, as designated at 510 above, is re-designated as the first feasible vector, and the summation value thereof is retained for comparative purposes. The method then proceeds back to 506 and a new other feasible vector is derived, processed and compared to the presently designated first feasible vector.

At 516, the sparse feasible vector, as designated at 510 above, is re-designated as the solution vector X. Thus, one instance of completing the method of the diagram 500 is complete.

The method of the diagram 500 is generally iterative in nature, usually—but not necessarily—requiring that a plurality R of feasible vectors $x_n$ be derived and compared in order to converge upon a final solution vector X for the echo data under consideration. The selected solution vector X, like the other feasible vectors $x_n$, satisfies Equation 1 above, but does so in accordance with an "L1 Norm Solution". That is, the solution vector X is selected in accordance with:

$$X=\arg\min\|x_n\|_1 \quad \text{(Equation 2)}$$

wherein all of the R feasible vectors $x_n$ are evaluated to find the solution vector X.

One of ordinary skill in the statistical arts will appreciate that the presently taught technique is distinct from the generally known "least squares" or "L2 Norm Solution" approach. The L1 Norm Solution is also referred to as "compressed sensing". One illustrative and non-limiting solution vector X is depicted in FIG. 4. As depicted, the solution vector X of FIG. 4 includes only respective component values of unity (i.e., 1) and zero. However, it is important to note that in general, the solution vectors X can have non-unity values.

Illustrative Data Plot

Figure 6:
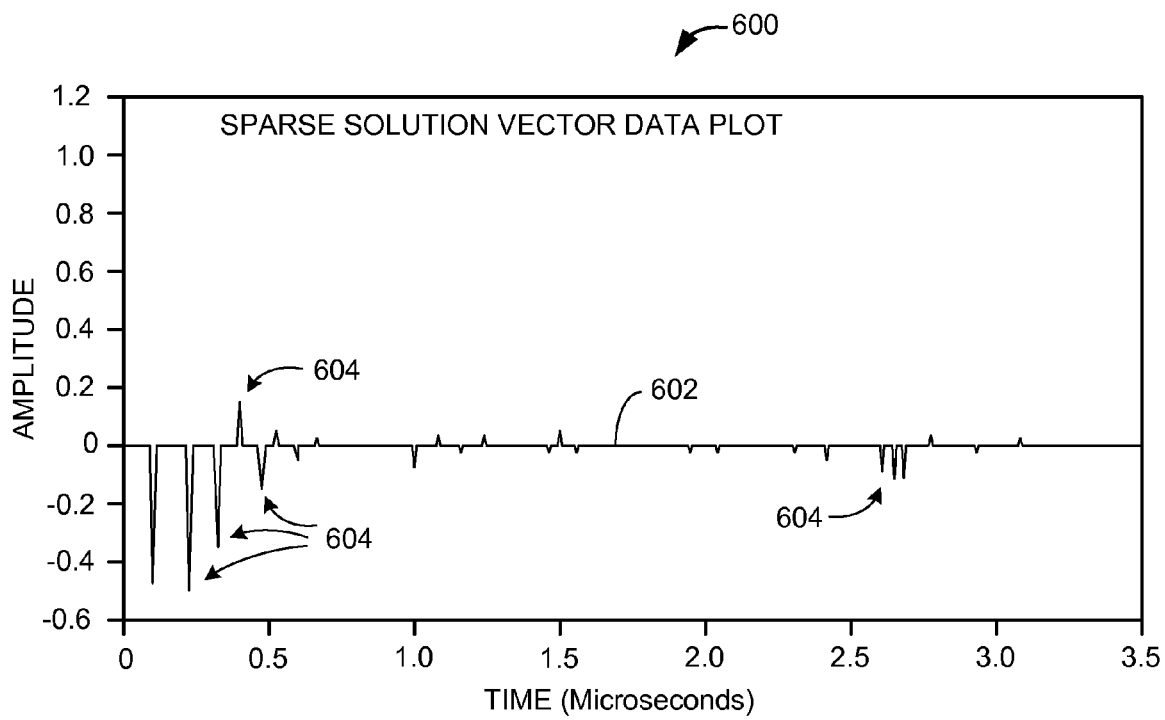
FIG. 6 is an illustrative signal timing diagram according to the present teachings.

FIG. 6 is a signal timing diagram 600 depicting a time-versus-amplitude plot of a solution vector (i.e., data) according to the present teachings. The diagram 600 is illustrative and non-limiting in nature, and is included in the interest of understanding the present teachings. The diagram 600 includes a time-domain signal 602 including numerous transients or "spikes" 604 corresponding to echoes detected during ultrasonic analysis of a laminate material. It is noted that the transients 604 are relatively distinct from one another, including readily discernable timing, amplitude and sign characteristics. Thus, the methods of the present teachings, wherein relatively long wavelength ultrasonic stimuli are used, result in solution vector data that lends itself to ready interpretation by the user. One of skill in the non-destructive testing arts will appreciate that the diagram 600 is not a B-scan display.

Illustrative System

Figure 7:
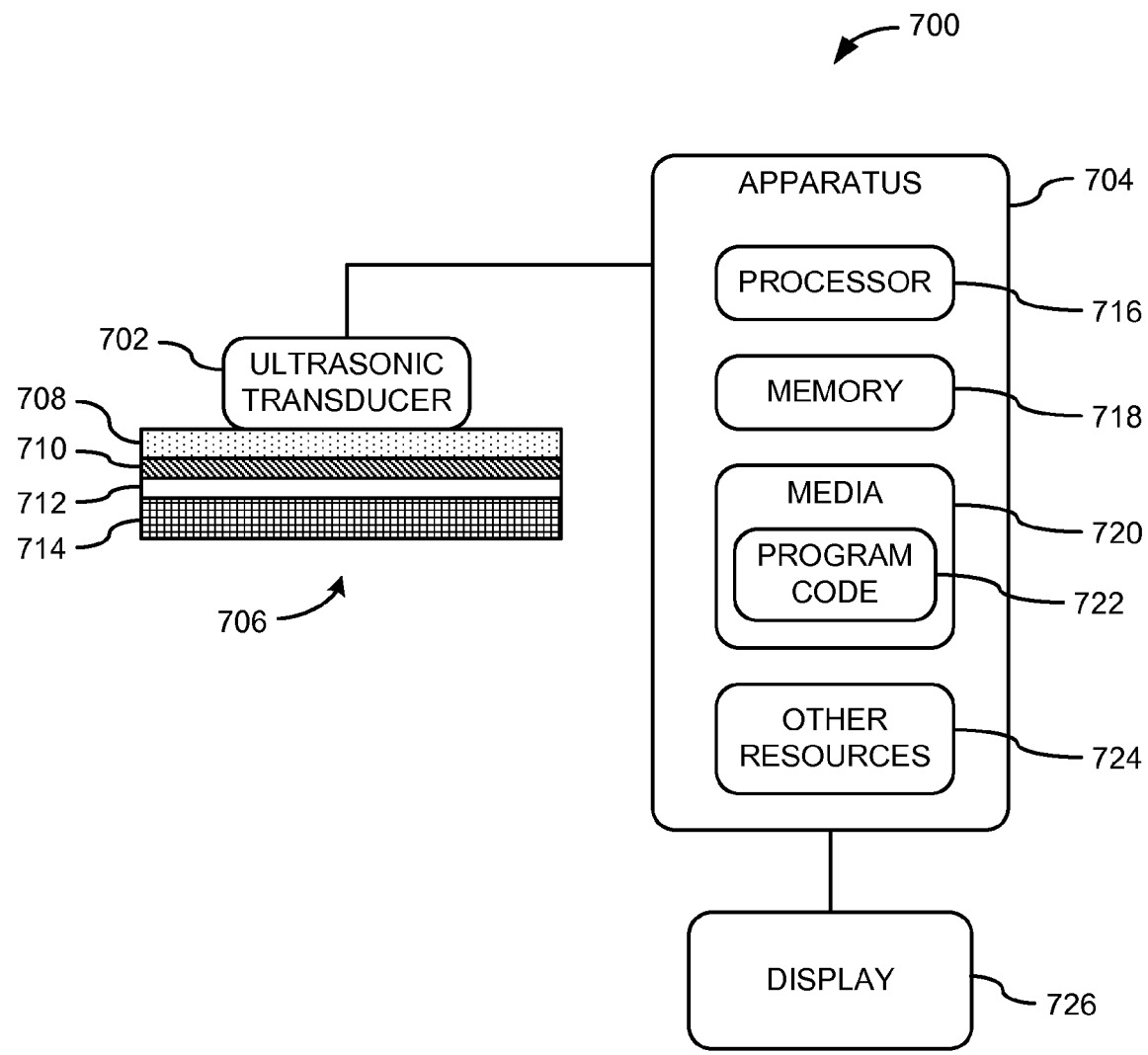
FIG. 7 is a block diagram depicting a system in accordance with an implementation.

FIG. 7 is a block diagrammatic view depicting an ultrasonic non-destructive testing system (system) 700 according to one illustrative and non-limiting implementation of the present teachings.

The system 700 includes an ultrasonic transducer 702. The ultrasonic transducer 702 is configured to produce an ultrasonic pulse (i.e., stimulus) of predetermined characteristics such as, for example, amplitude, wavelength, and so on. The ultrasonic transducer 702 is further configured to detect any echoes that occur responsive to a stimulus pulse emitted by the ultrasonic transducer 702. Such detected echoes are converted to corresponding electrical signals by the ultrasonic transducer 702 and communicated to an apparatus 704. The apparatus 704 is configured to control the operation of the ultrasonic transducer 702 and to receive echo signals there from. For purposes of non-limiting illustration, the ultrasonic transducer 702 is depicted in FIG. 7 as being in operative contact with a laminate structure 706, which includes respective material layers 708, 710, 712 and 714.

The apparatus 704 in the system 700 includes at least one processor 716, memory (i.e., computer-accessible storage) 718, and media 720 that includes program code 722. The processor(s) 716 is/are configured to operate, at least in part, in accordance with the program code included on media 720. In turn, the processor(s) 716 control(s) some, or all, of the operations and functions of the apparatus 704 including, among other things, operation of and communication with the transducer 702.

The memory 718 is configured to be accessible to the processor(s) 716 such that data may be stored within and retrieved from the memory 718. The memory 718 can be defined by any suitable data (i.e., information) storage apparatus. Non-limiting examples of such memory 718 include random access memory (RAM), non-volatile storage memory, an optical data storage device, a magnetic storage device (disk drive), electrically erasable programmable read only memory (EEPROM), etc. Other types of memory 718 may also be used.

The media 720, including the program code 722, can be defined by any suitable storage such as, for non-limiting example, random access memory (RAM), non-volatile solid-state storage memory, one or more optical data storage units (e.g., CD-ROM, DVD, etc.), one or more magnetic storage units (i.e., floppy disks and/or hard disks, etc.), electrically erasable programmable read only memory (EEPROM) devices, etc. Other types of media 720 may also be used. In any case, the media 720 is defined by one or more tangible, computer-accessible storage entities, of one or more types and/or configurations, which include program code compatible with the processor(s) 716.

The apparatus 704 further includes other resources 724 as required and/or desired for operations of the apparatus 704. Non-limiting examples of such resources 724 include digital-to-analog conversion (DAC) circuitry, analog-to-digital conversion (ADC) circuitry, a power supply or other energy source(s), a user interface, network communications resources, wireless communications resources, application specific integrated circuitry (ASIC), various electronic circuitry, and so on. One of skill in the instrumentation and related arts can appreciate that any suitable resources 724 can be included so as to enable some number of normal operations and functions of the apparatus 704. In at least one implementation, the apparatus 704 is defined, at least in part, by a computer.

The system 700 further includes an electronic display 726. The display 726 is coupled in signal communication with the apparatus 704 so as to receive information (signals) there from and to graphically and/or textually present that information to a user. In at least one implementation, the display 726 is configured to provide a B-scan display of ultrasonic echo information in accordance with the present teachings. The display 726 can also be configured to present other types and/or formats of information display.

The various elements of the system 700 are individually and cooperatively configured to perform at least some of the methods of the present teachings. For non-limiting example, the system 700 is configured to perform the methods depicted by FIGS. 3 and 5. Other suitable operations can also be performed by the system 700. In any case, the system 700 is illustrative and non-limiting with respect to the present teachings. For example, while only one ultrasonic transducer 702 is depicted, it is to be understood that any suitable number of transducers 702 may be used. In another example, and not by limitation, more than one electronic display 726 can be included for simultaneous display of non-destructive testing data.

While specific embodiments of the disclosure have been illustrated and described herein, as noted above, many changes can be made without departing from the spirit and scope of the disclosure. Accordingly, the scope of the disclosure should not be limited by the disclosure of the specific embodiments set forth above. Instead, the scope of the disclosure should be determined entirely by reference to the claims that follow.

What is claimed is:

1. A method performed at least in part by a computer, comprising:

recording pulse data corresponding to an ultrasonic pulse emitted into a multi-layer structure of a material by a transducer in a memory of a computer;

recording echo data resulting from the ultrasonic pulse in the memory of the computer;

defining a matrix "φ" including time-shifting the pulse data by predetermined amounts;

deriving an echo vector "Y" from the echo data;

determining a solution vector "X" within a predetermined tolerance in accordance with an expression: Y=φ*X; and presenting the solution vector X as a B-scan display that represents the multi-layer structure of the material on a display device.

2. The method of claim 1, further comprising identifying one or more anomalies in the multi-layer structure by way of the solution vector X or the B-scan display.

3. The method of claim 1, wherein the determining the solution vector X further comprises:

deriving a plurality of feasible vectors $x_n$ each comprising a plurality of component values; and selecting one of the feasible vectors $x_n$ as the solution vector X.

4. The method of claim 3, wherein the selecting one of the feasible vectors $x_n$ further comprises:

determining an absolute value of each of the component values for each of the feasible vectors $x_n$;

summing the absolute values for each of the feasible vectors $x_n$; and selecting one of the feasible vector having the minimum summation value as the solution vector X.

5. The method of claim 3, wherein the selecting one of the feasible vectors $x_n$ comprises selecting the solution vector X in accordance with the expression:

$$X = \arg\min \|x_n\|_1$$

wherein the feasible vectors $x_n$ are individually evaluated in order to determine the argument with minimum 1-norm value.

6. The method of claim 1, wherein the B-scan display comprises a plurality of distinct solution vectors X corresponding to a plurality of ultrasonic scans of the multi-layer structure.

7. The method of claim 1, wherein the ultrasonic pulse emitted by the transducer is incident to the multi-layer structure having one or more layers defined by respective thicknesses.

8. A system comprising a memory and a processor, the memory to store a plurality of computer-executable instructions for execution by the processor, the computer-executable instructions comprising:
   record pulse data corresponding to an ultrasonic pulse that is emitted into a multi-layer structure of a material;
   record echo data corresponding to one or more echoes resulting from the ultrasonic pulse;
   define a matrix "φ" including time-shifting the pulse data by predetermined amounts;
   derive an echo vector "Y" from the recorded echo data;
   determine a solution vector "X" within a predetermined tolerance in accordance with the expression: Y=φ*X; and
   present the solution vector "X" as a B-scan display that represents the multi-layer structure of the material on a display device.

9. The system of claim 8, wherein the instruction for determine a solution vector "X" further comprises instructions for:
   derive a plurality of feasible vectors $x_n$ each comprising plural component values; and
   select one of the feasible vectors $x_n$ as the solution vector X.

10. The system of claim 9, wherein the instruction for select one of the feasible vectors $x_n$ further comprises instructions for:
   determine an absolute value of each of the component values for each of the feasible vectors $x_n$;
   sum the absolute values for each of the plural feasible vectors $x_n$ to define a plurality of summation values; and
   select one of the feasible vector $x_n$ having the minimum summation value as the solution vector X.

11. The system of claim 9, wherein the instruction for select one of the feasible vectors $x_n$ further comprises instructions for select the solution vector X in accordance with the expression:

$X = \arg\min \|x_n\|_1$ wherein all of the plural feasible vectors $x_n$ are individually evaluated by the system in order to determine the argument with minimum one-norm value.

12. The system of claim 8, wherein the instructions for present includes instructions for present a plurality of distinct solution vectors X corresponding to a plurality of ultrasonic scans of the multi-layer structure as the B-scan display.

13. The system of claim 8, wherein the ultrasonic pulse is emitted by way of a transducer, the ultrasonic pulse being incident to the multi-layer structure during emission.

14. An apparatus comprising electronic circuitry, the apparatus comprising:
   a first component to obtain pulse data corresponding to an ultrasonic pulse emitted into a multi-layer structure of a material by a transducer;
   a second component to obtain echo data resulting from the ultrasonic pulse;
   a third component to derive one or more vectors including time-shifting the obtained pulse data by respective amounts;
   a fourth component to define a matrix "φ" including the one or more vectors;
   a fifth component to derive an echo vector "Y" from the obtained echo data;
   a sixth component to determine a solution vector "X" within a predetermined tolerance in accordance with the expression: Y=φ*X, the solution vector X stored at least temporarily in a memory of the apparatus; and
   a seventh component to present the solution vector X as a B-scan display that represents the multi-layer structure of the material on a display device.

15. The apparatus of claim 14, wherein the sixth component is to further:
   derive a plurality of feasible vectors each comprising plural component values; and
   select one of the feasible vectors as the solution vector X.

16. The apparatus of claim 15, wherein the sixth component is to further:
   determine absolute values of the component values for each of the feasible vectors;
   sum the absolute values for each of the feasible vectors to define a plurality of summation values; and
   select the feasible vector having the minimum summation value of as the solution vector X.

17. The apparatus of claim 16 wherein the selecting the feasible vector comprises:
   select the solution vector X in accordance with the expression:

$X = \arg\min \|x_n\|_1$ wherein all of the plural feasible vectors $x_n$ are individually evaluated by the system in order to determine the argument with minimum one-norm value.

18. A computer-readable storage media storing computer-executable instructions that when executed, cause one or more processors to perform acts comprising:
   derive one or more vectors including time-shifting a recorded pulse data by respective amounts, the recorded pulse data being derived from an ultrasonic pulse emitted into a multi-layer structure of a material;
   define a matrix "φ" including the one or more vectors;
   derive an echo vector "Y" from a recorded echo data;
   determine a solution vector "X" within a predetermined tolerance in accordance with the expression: Y=φ*X, the solution vector X stored at least temporarily in a memory accessible by the one or more processors; and
   present the solution vector X as a B-scan display that represents the multi-layer structure of the material on a display device.

19. The computer-readable storage media of claim 18, wherein the determine a solution vector "X" further comprises:
   derive a plurality of feasible vectors each comprising plural component values and
   select one of the feasible vectors as the solution vector X.

20. The computer-readable storage media of claim 19, wherein the select one of the feasible vectors comprises:
   determine an absolute value of each of the component values for each of the feasible vectors;
   sum the absolute values for each of the feasible vectors to define a plurality of summation values; and
   select the feasible vector having the minimum summation value as the solution vector X.

* * * * *